United States Patent [19]

Bander et al.

[11] Patent Number: 4,713,352

[45] Date of Patent: Dec. 15, 1987

[54] MONOCLONAL ANTIBODY PANEL FOR EARLY DIAGNOSIS AND THERAPY OF RENAL CARCINOMA

[75] Inventors: Neil H. Bander; Willet F. Whitmore; Lloyd J. Old, all of New York, N.Y.

[73] Assignee: Sloan-Kettering Institute for Cancer Reseach, New York, N.Y.

[21] Appl. No.: 607,168

[22] Filed: May 4, 1984

Related U.S. Application Data

[63] Continuation-in-part of Ser. No. 297,814, Aug. 31, 1981, Pat. No. 4,650,765.

[51] Int. Cl.$^4$ .................. G01N 33/53; G01N 33/566
[52] U.S. Cl. .................................. 436/548; 436/501; 436/811; 436/813; 530/387; 424/85
[58] Field of Search ............... 436/548, 813, 501, 811; 424/85; 530/387

[56] References Cited

PUBLICATIONS

Ueda, R. et al, (1981), Proc. Natl. Acad. Sci. USA, 78, No. 8: 5122–5126.

Fradet, Y. et al., (1984), Proc. Natl. Acad. Sci. USA, 81: 224–228.

Lennox, E. et al, (1982), in "Monoclonal Antibodies in Medicine" (McMichael and Fabre, Eds), Academic Press, Chapter 5, pp. 111–128.

*Primary Examiner*—Sidney Marantz
*Assistant Examiner*—Jack Spiegel
*Attorney, Agent, or Firm*—John P. White

[57] ABSTRACT

A panel of monoclonal antibodies is developed for use in diagnosis and treatment of renal carcinoma. One monoclonal antibody $F_{31}$ reacts with 80% of renal carcinoma. The area of overlap of reactivity of monoclonal antibodies $F_{31}$, $F_{23}$, $S_4$, $S_{23}$ and $S_{27}$ is the site of origin of most renal carcinomas. Reactivity with this panel of monoclonal antibodies localizes most renal carcinoma and is a vehicle for early diagnosis and treatment.

5 Claims, No Drawings

MONOCLONAL ANTIBODY PANEL FOR EARLY DIAGNOSIS AND THERAPY OF RENAL CARCINOMA

The invention was made in part with government support under CA 08748 awarded by the National Cancer Institute. The government has certain rights in this invention.

This application is a continuation-in-part of U.S. Ser. No. 297,814, filed Aug. 31, 1981, now U.S. Pat. No. 4,650,765, issued Mar. 17, 1987, the contents of which are hereby incorporated by reference.

The present invention relates to a method of using monoclonal antibodies and their antigenic specificities in identifying, characterizing as well as determining a prognosis for human renal cancers. This is a useful diagnostic tool in the detection and clinical prognosis of renal cancer as well as the study of the nature of renal cancer. Antigenic profiles offer insight into prognosis for renal cancer types.

Red blood cells, immunofluorescent, radioactive or enzymatic tagging agents can be bound to the highly specific antibodies using normal procedures, as required for indexing methods. Cytotoxic or cytostatic agents can also be bound to the highly specific antibodies to produce so called "magic bullet" type therapeutic agents which selectively destroy the cells with which the specific antibody binds.

BACKGROUND

In 1975 Köhler and Milstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Köhler-Milstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man and is relatively advanced. (See Pat. Nos. 4,361,549–550; 4,364,932–37 and 4,363,799 concerning mAb to Human T-cell antigens). Little is known about differentiation antigens displayed on normal and neoplastic cells belonging to other lineages.

This is due to the difficulty of obtaining a ready source of the appropriate normal cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens.

We recently described our initial analysis of cell surface antigens of human malignant melanoma identified by mouse monoclonal antibodies (Abs) (Dippold et al. Proc. Natl. Acad. Sci. USA 77, 6114–6118 (1980)). This invention relates to a comparable analysis of human renal cancer. Previous work is found in a co-pending patent application Ser. No 297,814 Monoclonal Antibodies To Cell Surface Antigens of Human Renal Cancer and Ser. No. 474,224 Monoclonal Antibodies to Human Renal Cancer Antigens and Method.

Seventeen monoclonal antibodies derived from fusions with spleen cells of mice immunized with established culture lines of renal cancers identified nine cell surface antigenic systems (Ueda, Ryuzo et al, Proc. Natl. Acad. Sci. USA, 78, 5112 August 1981) Six of the systems gp160, $S_{25}$, gp120r, gp120nr, gp115, and $V_1$ represented new antigens not previously described. The other three systems were related to HLA—A, —B, and —C heavy chain and A and B blood group antigens. The most restricted of the newly described antigens were gp160, $S_{25}$, gp140 and gp120r. These determinants are found only on cells of renal origin, both normal and malignant, and represent differentiation antigens of human kidney. In addition to the difference in the molecular weight of two of these antigens, gp160, $S_{25}$, and gp120r can be distinguished on the basis of differential expression on a panel of cultured renal cancers and normal kidney epithelium and fetal kidney cells. Glycoproteins bearing gp120r share a determinant with renal gp120nr (as indicated by sequential precipitations with monoclonal antibodies that detect gp120r and gp120nr), but gp120nr is found on a broader range of cell types, including fibroblasts and cell lines derived from ovarian, bladder, and colon cancers. The two other systems, gp115 and $V_1$, have characteristics of broadly occurring differentiation antigens but can be distinguished from each other and from gp120nr by differences in molecular weight, heat stability ($V_1$ is a heat-stable determinant), and differential expression on cell types of diverse origin.

These systems can be used to characterize and study the nature of renal cancer. Thus, comparison of the $S_{25}$ and gp160 phenotypes of different renal cancer cell lines and cultures of normal kidney clearly distinguish these two systems.

The study of renal cancer Old, et al., supra, co-pending Ser. No. 297,814 of melanoma (Dippold, et al Proc. Natl. Acad. Sci. USA 77, 6114 (1980)), has generated a series of mouse Abs that defined 12 new systems of human cell surface antigens. Six of these had been identified as glycoproteins (gp95, gp150, gp160, gp120r, gp120nr, and gp115), three are heat-labile antigens that could not be immunoprecipitated from labeled cell extracts ($S_{25}$, $M_{19}$, and $R_8$), and three are heat-stable antigens, presumably glycolipids ($O_5$, $R_{24}$, and $V_1$). The use of a standard panel of cultured human cells allows, ready comparisons of the reactivity of these monoclonal antibodies in direct serological tests and absorption analysis, and each of the antigenic systems has a distinct pattern of distribution on the cell panel, in terms of both qualitative and quantitative expression of antigens. On the basis of their distribution on different cell types, these 12 antigenic systems can be further classified into three groups: (i) those with characteristics of restricted differentiation antigens (e.g., the renal-specific gp160, $S_{25}$, and gp120r antigens and the $R_{24}$ antigen of melanoma and melanocytes), (ii) more broadly represented differentiation antigens (e.g., gp95, gp150, $M_{19}$, gp120nr, and $V_1$, and (iii) antigens expressed by every human cell type tested (e.g., $O_5$ species antigen).

It has also been found that the cell lines derived from stage I renal cancer (confined to the kidney) are gp160+, whereas cell lines from metastatic renal cancers are gp160−. Whether this indicates that cancer cells developing metastatic potential lose gp160 expression, or that gp160+ and gp160− renal cancers are derived from separate cell lineages is not determined; however, identifying the cell types in normal kidney that express gp160 and other antigens found on renal cancer should give information about the cellular origins of renal cancer.

These serological probes provided by the invention can identify kidney-specific antigens and are of particular interest in the study of kidney structure and function. In addition, some of the more broadly reacting antibodies are useful in studying other tumors —e.g. $V_1$ which distinguishes astrocytomas from melanomas.

The importance of parallel biochemical and serological characterizations of antigens identified by Abs is illustrated by the analysis of gp120r and gp120nr. Five Abs in this series immunoprecipitated a 120,000-dalton component from labeled extracts of SK-RC-7 renal cancer cells. Pre-clearing the extract with one of these Abs (AB $S_6$) removed the 120,000-dalton component identified by Ab $S_{23}$, indicating that the two Abs were reacting with the same molecule. However, the antigenic determinant detected by Ab S6 and Ab $S_{23}$ can be distinguished in M-MHA tests and absorption analysis. Ab $S_{23}$ detected a kidney-specific antigen, whereas Ab $S_6$ reacted with a much broader range of cell types. These results can be explained by postulating two species of gp120 molecules, both carrying the epitope identified by Ab $S_6$ but only one with the epitope identified by Ab $S_{23}$. In agreement with this interpretation, supernatants after clearing with Ab $S_{23}$ still reacted with Ab $S_6$, even though no antigen precipitating with Ab $S_{23}$ remained. The epitope identified by Ab $S_{23}$ is found only on cells of renal origin, and, because of this restricted distribution, it is referred to as gp120r. The more widely distributed epitope has been designated "nr" to indicate its nonrestricted nature. gp120r and gp120nr may be the products of two separate genes or of a single gene whose product is modified in renal cells. Similar, although less striking, discrepancies in the cellular distribution of antigens identified by different monoclonal antibodies immunoprecipitating gp95 or gp150 molecules have also been explained on the basis of different epitopes being recognized (Dippold, et al. Proc. Natl. Sci. USA 77, 6114–6118 (1980)).

SUMMARY

Renal carcinomas can be typed with monoclonal antibodies leading to renal carcinoma subsets. New monoclonal antibodies which may be labeled with a fluorescent or radioactive agent, can be used in a method to determine histiogenesis as well as prognosis of renal carcinoma subsets. Localization of a site where most renal carcinomas probably arise is probed with monoclonal antibodies. A new monoclonal antibody $F_{31}$ is described herein.

DESCRIPTION

Techniques:

Tissue Culture. The renal cancer cell lines (Ueda et al J. Exp. Med. 150, 564–589 (1979)) and tumor cell lines (Carey, et al Proc. Natl. Acad. Sci. USA 73, 3278–3282 (1976)) have been described. Methods for the short-term culture of normal kidney epithelium have also been described (Ueda (supra)). Cultures were maintained in Eagle's minimal essential medium supplemented with 2 mM glutamine, 1% nonessential amino acids, 100 units of penicillin per ml, 1 microgram of streptomycin per ml, and 10% (vol/vol) fetal bovine serum. Cultures were regularly tested for mycoplasma, fungi, and bacteria, and contaminated cultures were discarded. SK-RC-7 serves as the immunizing cell line to derive mAbs $S_4$, $S_{22}$, $S_{23}$, and $S_{27}$.

Serological Procedures. The mouse mixed hemadsorption assay (M-MHA) was performed by the method of Fagraeus et al. Immunology 9, 161–175 (1965), as modified to detect mouse antibody (Metzgar, R. S., et al. (1968) Cancer Res. 28:1366). Serological procedures for direct test and absorption analysis are described in Dippold et al (supra); Ueda et al (supra) and Carey et al (supra). Briefly, as described by Carey, Supra, cultured cells were harvested, washed and distributed to the wells (1000 cells per well) of 3040 microtest II plates (Falcon Plastics, Oxnard, Calif.) and the plates were incubated at 37° in a $CO_2$ incubator. Multiple plates were prepared for each test and examined in MHA assays at several different time intervals after cell passage to insure detection of surface antigens with variable expression.

Serum dilutions were prepared in phosphate-buffered saline (Pi/NaCl) containing 5% FCS. The medium was decanted from the test plates and 0.05 ml of each serum dilution was added to replicate wells. The plates were then incubated at room temperature for 45 min and washed three times with Pi/NaCl—FCS. Indicator human O red blood cells were suspended in Pi/NaCl—FCS (0.2% vol/vol) and 0.1 ml aliquots were added to each well. The plates were again incubated at room temperature for 45 min, agitated gently, washed three times in Pi/NaCl—FCS, and examined under a light microscope. Each well was scored for percent positive target cells, and for the intensity of the reaction. A cell was considered positive when ¼ or more of its perimeter was covered by indicator cells. For a well to be scored positive, 5% or more positive cells needed to be present. (This represents a stringent criteria as 1% positive cells in a well could usually be detected without question).

The absorption procedure according to Old et al. [Old, L. J., (1965) Cancer Res. 25:813] as described by Carey, Supra is as follows:

On the day of the absorption test, the serum to be examined was titrated against target cells by MHA and the dilution yielding 25% positive cells was determined. A dilution of serum two doubling dilutions below this end-point was prepared. One aliquot remained unabsorbed, while other aliquots were each mixed with an equal volume of packed cells. (In order to avoid possible enzymatic destruction of surface antigens, cultured cells used for absorption were harvested by mechanical scraping). Absorptions were carried out, with frequent mixing, first at room temperature for 45 min. and then on ice for an equal period. The absorbing cells were then removed by centrifugation, and the absorbed and unabsorbed sera were serially diluted and tested against the target cells.

Immunofluorescence Technique

Using methods established in the prior art, for example: Frozen sections (5 micrometer) of tissues were fixed 5 min in 3.7% formaldehyde in phosphate-buffered saline (PBS), washed and incubated for 1 hr with undiluted hybridoma culture supernatants. The slides were washed and incubated for 30 min with a 1:40 dilution of fluorescein conjugated goat anti-mouse Ig (Cappel Laboratories, Cochranville, Pa.), washed again and wet-mounted in 90% glycerol in PBS. (See Fradet, Y., et al. Proc. Nat'l. Acad. Sci. USA (1984) 81:224).

Peroxidase Technique
using standard methods established in the prior art.

Immunizations. (BALB/C×C57BL/6)F$_1$ female mice were immunized with established renal cancer cell line SK-RC-7. For the initial immunization, 1×10$^7$ renal cancer cells were injected subcutaneously without adjuvant. Subsequent immunizations were carried out at intervals of 3–4 weeks by intraperitoneal inoculation of 1×10$^7$ renal cancer cells. Immunized mice were sacrificed 3 days after the last immunization.

Derivation of Mouse Abs. The fusion of immune spleen cells with mouse myeloma MOPC-21 NS/1 cells was performed as described (Dippold et al (supra) and Kohler & Milstein, Nature (London) 236, 495–497 (1975). Fused cells (5-8 ×10$^5$) in 1 ml of selective medium containing hypoxanthine, aminopterin, and thymidine were added to wells of tissue culture plates (Costar no. 3524, 24 wells per plate). Hybridoma cultures were subcloned at least three times by limiting dilution on a feeder layer of 1–3×10$^5$ mouse peritoneal macrophages. Culture supernatants were monitored for antibody activity on a panel of cultured cells consisting of two renal cancer cell lines (including the immunizing line), AJ astrocytoma, SK-MEL-33 and -37 melanomas, Me-180 cervix cancer, WI-38 fetal cells, VERO adult and fetal kidney epithelium, and fetal brain cells. Antibody subclass was determined by double diffusion in agar with anti-Ig heavy chain specific reagents (Bionetics, Kensington, M. D.). Cultures of cloned hybridomas were injected subcutaneously into nu/nu mice (Swiss background) and were also stored in liquid nitrogen. Sera from mice with progressively growing tumors were collected, stored at −70° C., and used for serological and biochemical characterization.

Immunoprecipitation Procedures. Cells were metabolically labeled with [$^3$H]glucosamine in complete Eagle's medium containing 15 uCi of [$^3$H] glucosamine (New England Nuclear; 30–60 Ci/mmol; 1 Ci=3.7×10$^{10}$ becquerels) per ml for 48 hr at 37° C.; the labeled cells were extracted with 0.5% Nonidet P-40 (NP-40) in Tris buffer as described (Ogata et al. Proc. Natl. Acad. Sci. USA 78, 770–774 (1981)) except that the 3 M KCl treatment was omitted. Immunoprecipitation was carried out by mixing a portion of the cell extract (1×10$^5$ cpm) with 2 ul of mouse serum and 20 ul of rabbit anti-mouse Ig serum (Cappel Laboratories, Cochranville, Pa.) in Tris buffer). Immune complexes were isolated by using *Staphylococcus aureus* and analyzed by NaDodSO$_4$/ polyacrylamide gel electrophoresis as described (Dippold et al (supra)). [$^{35}$S] Methionine-labeled samples were immunoprecipitated in a similar manner, except that Sepharose-rabbit F (ab')$_2$ anti-mouse Ig was used for isolating the complexes. To determine the pI of the antigens, immunoprecipitates were examined by two-dimensional electrophoresis by the O -Farrell procedure (O'Farrell, P. H. Biol. Chem. 250, 4007–4021 (1975)) modified as described (Ogata, et al (supra)). From the five fusions of NS-1 myeloma with three different renal cancer cell lines, 17 antibody-producing clones were selected for detailed analysis (Table 1). The serological specificity of these antibodies was tested on a panel of 47 established cell lines [13 renal cancers, 5 melanomas, gliomas neuroblastomas, 15 epithelial cancers 5 B-cell lines K562 (an erythroid leukemia), 2 T-cell lines (MOLT-4 and T-45), and monkey kidney cells (VERO)]. In addition, the antibodies were tested against short-term cultures of normal kidney epithelium, fibroblasts, and fetal tissues (brain, fibroblasts, and kidney). Human, sheep, rat and bovine erythrocytes were also examined. In most cases, serological analysis consisted of both direct and absorption tests. See Table IA for serological analysis of representative monoclonal antibodies and Table IB for specific titers.

These serological studies in conjunction with immunochemical analysis defined nine distinct antigenic systems. Three systems (gp160, S$_{25}$, and gp120) were restricted to normal and malignant renal cells, three systems (gp120nr, gp115, and V$_1$) were more widely distributed, and three systems were identified as HLA—A, —B, —C heavy chain and A and B blood group antigens.

In frozen section (Table II) S4, S6, S22, S23, and S27 shown specificity for kidney tissue. Serological tests shows specificity for kidney tumor (Table IA & B).

TABLE IA

| SEROLOGICAL REACTION OF mAbs PRODUCED FROM HUMAN RENAL TUMORS AND NORMAL EPITHELIUM AS IMMUNOGEN WITH VARIOUS CANCER CELL LINES AND NORMAL CELL LINES | | | | | | | | | | |
|---|---|---|---|---|---|---|---|---|---|---|
| | *S4 | *S25 | *S22 | *S23 | *S6 | *S27 | *V1 | *S21 | F23 | *M2 | *S8 |
| Ig class of | γ2a | γ1 | γ1 | γ1 | γ1 | γ1 | γ1 | γ1 | γ2a | μ | μ |

TABLE IA-continued
SEROLOGICAL REACTION OF mAbs PRODUCED FROM HUMAN RENAL TUMORS AND NORMAL EPITHELIUM AS IMMUNOGEN WITH VARIOUS CANCER CELL LINES AND NORMAL CELL LINES

| antibody: | *S4 | *S25 | *S22 | *S23 | *S6 | *S27 | *V1 | *S21 | F23 | *M2 | *S8 |
|---|---|---|---|---|---|---|---|---|---|---|---|
| Antigen detected: | gp160 | | gp115 | gp120r | gp120nr | gp120nr | gp45 β2 | gp140 | | | |
| CELLS TESTED | | | | | | | | | | | |
| Renal Cell Lines | | | | | | | | | | | |
| *SK-RC-1 | 3 | 1 | 1 | 2 | 3 | 3 | 3 | 3 | | | |
| *SK-RC-2 | 0 | 0 | 1 | 0 | 3 | 3 | 3 | 3 | | | |
| *SK-RC-4 | 3 | 3 | 3 | 3 | 3 | 3 | 3 | 3 | 0 | 0 | 2 |
| *SK-RC-6 | 3 | 0 | 2 | 3 | 3 | 3 | 3 | 3 | | | |
| *SK-RC-7 | 3 | 3 | 3 | 2 | 3 | 3 | 3 | 3 | 1 | 0 | 2 |
| *SK-RC-8 | 0 | 2 | 3 | 2 | 3 | 3 | 3 | 3 | | | |
| *SK-RC-9 | 0 | 1 | 3 | 1 | 3 | 3 | 3 | 3 | | | |
| *SK-RC-11 | 2 | 1 | 1 | 2 | 3 | 3 | 3 | 3 | | | |
| SK-RC-12 | 3 | | 0 | 2 | | 3 | | | 0 | | |
| SK-RC-13 | 3 | | 0 | 2 | | 3 | | | 0 | | |
| SK-RC-15 | 3 | | 0 | 3 | | 3 | | | 0 | | |
| SK-RC-16 | 2 | | 0 | 1 | | 3 | | | 0 | | |
| SK-RC-17 | 0 | | 0 | 0 | | 3 | | | 2 | | |
| SK-RC-18 | 2 | | 0 | 0 | | 3 | | | 2 | | |
| SK-RC-20 | 1 | | 0 | 1 | | 3 | | | 1 | | |
| *SK-RC-21 | 0 | 0 | 1 | 0 | 3 | 3 | 2 | 3 | 1 | | |
| SK-RC-24 | 3 | | 0 | 2 | | 3 | | | 3 | | |
| SK-RC-26a | 2 | | 1 | 1 | | 3 | | | 0 | | |
| SK-RC-26b | 3 | | 0 | 1 | | 3 | | | 0 | | |
| *SK-RC-28 | 3 | 1 | 1 | 3 | 3 | 3 | 3 | 3 | | 2 | 0 |
| *SK-RC-29 | 0 | 0 | 1 | 0 | 3 | 3 | 3 | 3 | | | |
| SK-RC-33 | 2 | | 2 | 2 | | 3 | | | 3 | | |
| SK-RC-34 | 3 | | 3 | 3 | | 3 | | | 2 | | |
| SK-RC-35 | 3 | | 3 | 3 | | 3 | | | 3 | | |
| CELLS TESTED | | | | | ANTIBODY | | | | | | |
| Renal Cell lines | | | | | | | | | | | |
| SK-RC-37 | 1 | | 0 | 1 | | 3 | | | 2 | | |
| SK-RC-38 | 3 | | 0 | 3 | | 3 | | | 2 | | |
| SK-RC-39 | 3 | | 1 | 3 | | 3 | | | 3 | | |
| SK-RC-40 | 3 | | 2 | 3 | | 3 | | | 3 | | |
| SK-RC-41 | 2 | | 0 | 3 | | 3 | | | 2 | | |
| SK-RC-42 | 0 | | 0 | 0 | | 3 | | | 2 | | |
| SK-RC-44 | 3 | | 1 | 2 | | 3 | | | 1 | | |
| SK-RC-45 | 3 | | 0 | 3 | | 3 | | | 3 | | |
| SK-RC-46 | 3 | | 0 | 0 | | 3 | | | 0 | | |
| A-498 | 3 | 0 | 1 | 1 | 3 | 3 | 3 | 3 | | | |
| CaKi-1 | 0 | 0 | 1 | 0 | 3 | 3 | 3 | 3 | | | |
| Normal kidney epithelium | | | | | | | | | | | |
| NK-LI | 3 | | 2 | 2 | | 3 | | | 2 | | |
| NK-LD | 2 | | 0 | 1 | | 3 | | | 1 | | |
| *NK-ID | | 0 | 2 | 0 | 2 | 2 | 2 | 3 | | | |
| *NK-EQ | 3 | 0 | 2 | 0 | 2 | 2 | 2 | 3 | | | |
| *NK-HY | 3 | 0 | 2 | 0 | 2 | 2 | 2 | 3 | | | |
| *NK-GM | 2 | 2 | 2 | 0 | 2 | 2 | 2 | 3 | | | |
| *NK-FR | 2 | 2 | 2 | 0 | 2 | 2 | 2 | 3 | | | |
| *NK-EI | 2 | 1 | 2 | 0 | 2 | 2 | 2 | 3 | | | |
| *NK-IJ | 2 | 1 | 2 | 0 | 2 | 2 | 2 | 3 | | | |
| *NK-EG | 2 | 0 | 2 | 0 | 2 | 2 | 2 | 3 | | | |
| *NK-GR | 2 | 0 | 2 | 0 | 2 | 2 | 2 | 3 | | | |
| *NK-IB | 2 | 0 | 2 | 0 | 2 | 2 | 2 | 3 | | 0 | 2 |
| Normal fetal kidney cells | | | | | | | | | | | |
| *FK-C4 | 2 | 2 | 2 | 0 | 2 | 2 | 2 | 3 | | | |
| *FK-C6 | 0 | 2 | 2 | 0 | 2 | 2 | 2 | 3 | | | |
| *FK-C8 | 2 | 2 | 2 | 0 | 2 | 2 | 2 | 3 | | | |
| CELLS TESTED | | | | | | | | | | | |
| Epithelial cancer cell lines | | | | | | | | | | | |
| Bladder cell lines | | | | | | | | | | | |
| *RT-4 | 0 | 0 | 1 | 0 | 0 | 0 | 3 | 3 | | | |
| *5637 | 0 | 0 | 1 | 0 | 0 | 0 | 0 | 3 | | | |
| *T-24 | 0 | 0 | 1 | 0 | 2 | 2 | 0 | 3 | | | |
| *253J | 0 | 0 | 1 | 0 | 2 | 2 | 3 | 3 | | 2 | 0 |
| Breast cell lines | | | | | | | | | | | |
| *AlAb | 0 | 0 | 0 | 0 | 0 | 0 | 2 | 3 | | | |
| *BT-20 | 0 | 0 | 0 | 0 | 0 | 0 | 0 | 3 | | | |
| *MCF-7 | 0 | 0 | 0 | 0 | 0 | 0 | 3 | 3 | | | |
| *SK-BR-3 | 0 | 0 | 0 | 0 | 0 | 0 | 3 | 3 | | 0 | 2 |
| Cervix cell line | | | | | | | | | | | |
| *ME-180 | 0 | 0 | 0 | 0 | 0 | 0 | 1 | 1 | | 2 | 0 |

TABLE IA-continued
SEROLOGICAL REACTION OF mAbs PRODUCED FROM HUMAN RENAL TUMORS AND NORMAL EPITHELIUM AS IMMUNOGEN WITH VARIOUS CANCER CELL LINES AND NORMAL CELL LINES

|  | *S4 | *S25 | *S22 | *S23 | *S6 | *S27 | *V1 | *S21 | F23 | *M2 | *S8 |
|---|---|---|---|---|---|---|---|---|---|---|---|
| Colon cell lines |  |  |  |  |  |  |  |  |  |  |  |
| *HT-29 | 0 | 0 | 0 | 0 | 2 | 2 | 1 | 3 |  | 2 | 0 |
| *SW-1222 | 0 | 0 | 0 | 0 | 0 | 0 | 3 | 2 |  | 2 | 0 |
| Lung cell lines |  |  |  |  |  |  |  |  |  |  |  |
| *SK-LC-LL | 0 | 0 | 1 | 0 | 0 | 0 | 2 | 2 |  |  |  |
| *SK-LC-6 | 0 | 0 | 0 | 0 | 3 | 3 | 3 | 3 |  |  |  |
| Ovary cell line |  |  |  |  |  |  |  |  |  |  |  |
| *SK-CV-3 | 0 | 0 | 2 | 0 | 0 | 0 | 1 | 3 |  |  |  |
| Normal cell lines |  |  |  |  |  |  |  |  |  |  |  |
| *Adult skin fibroblast | 0 | 0 | 0 | 0 | 2 | 2 | 0 | 2 |  |  |  |
| *Fetal lung fibroblast | 0 | 0 | 2 | 0 | 2 | 2 | 2 | 3 | 3 |  |  |
| CELLS TESTED |  |  |  |  |  |  |  |  |  |  |  |
| Neuroectoderm cancer cell lines |  |  |  |  |  |  |  |  |  |  |  |
| Astrocytoma |  |  |  |  |  |  |  |  |  |  |  |
| *SK-MG-1 | 0 | 0 | 1 | 0 | 0 | 0 | 0 | 3 |  |  |  |
| *SK-MG-4 | 0 | 0 | 1 | 0 | 0 | 0 | 0 | 3 |  |  |  |
| *SK-MG-7 | 0 | 0 | 1 | 0 | 0 | 0 | 0 | 3 |  |  |  |
| Melanoma |  |  |  |  |  |  |  |  |  |  |  |
| *SK-MEL-13 | 0 | 0 | 0 | 0 | 0 | 0 | 3 | 3 |  |  |  |
| *SK-MEL-19 | 0 | 0 | 0 | 0 | 0 | 0 | 3 | 1 |  |  |  |
| *SK-MEL-28 | 0 | 0 | 0 | 0 | 0 | 0 | 3 | 3 |  |  |  |
| *SK-MEL-29 | 0 | 0 | 0 | 0 | 0 | 0 | 3 | 3 |  |  |  |
| *SK-MEL-37 | 0 | 0 | 0 | 0 | 0 | 0 | 3 | 3 |  |  |  |
| *SK-MEL-41 | 0 | 0 | 0 | 0 | 0 | 0 | 3 | 3 |  |  |  |
| Neuroblastoma |  |  |  |  |  |  |  |  |  |  |  |
| *SK-NMC | 0 | 0 | 0 | 0 | 0 | 0 | 2 | 3 |  |  |  |
| *SK-NSH | 0 | 0 | 0 | 0 | 0 | 0 | 2 | 3 |  |  |  |
| Normal primary cultures |  |  |  |  |  |  |  |  |  |  |  |
| *Fetal brain | 0 | 0 | 5 | 0 | 4 | 4 | 4 | 3 |  |  |  |
| #Fetal melanocytes | 0 | 0 | 0 | 3 | 3 |  | 3 | 3 |  |  |  |
| #Adult melanocytes | 0 | 0 | 0 | 3 | 3 |  | 3 | 3 |  |  |  |
| CELLS TESTED |  |  |  |  |  |  |  |  |  |  |  |
| Hematopoetic cancer cell lines |  |  |  |  |  |  |  |  |  |  |  |
| Lymphoblastoid cells |  |  |  |  |  |  |  |  |  |  |  |
| *EBV B cells - AX | 4 | 4 | 4 | 4 | 4 | 4 | 5 | 5 |  |  |  |
| *EBV B cells - BE | 4 | 4 | 4 | 4 | 4 | 4 | 5 | 5 |  |  |  |
| *EBV B cells - EU | 4 | 4 | 4 | 4 | 4 | 4 | 5 | 5 |  |  |  |
| *Burkitt's Lym - Daud. | 4 | 4 | 4 | 4 | 4 | 4 | 5 | 5 |  |  |  |
| *Burkitt's Lym - Raji | 4 | 4 | 4 | 4 | 4 | 4 | 5 | 5 |  |  |  |
| +Cells - Molt-4 | 4 | 4 | 4 | 4 | 4 | 4 | 4 | 5 |  |  |  |
| *T cells - T-45 | 4 | 4 | 4 | 4 | 4 | 4 | 4 | 5 |  |  |  |
| Normal cells |  |  |  |  |  |  |  |  |  |  |  |
| *Erythrocytes - A | 4 | 4 | 4 | 4 | 4 | 4 | 4 | 4 | 4 | 3 | 0 |
| *Erythrocytes - B | 4 | 4 | 4 | 4 | 4 | 4 | 4 | 4 | 4 | 0 | 3 |
| *Erythrocytes - O | 4 | 4 | 4 | 4 | 4 | 4 | 4 | 4 | 4 | 0 | 0 |
| Xenogeneic cells |  |  |  |  |  |  |  |  |  |  |  |
| *Monkey kidney VERO | 0 | 0 | 0 | 0 | 3 | 0 | 0 | 0 |  |  |  |
| *Sheep erythrocytes | 4 | 4 | 4 | 4 | 4 | 4 | 4 | 4 |  | 0 | 0 |

References
*Ueda, R., Ogata, S.-I., Morrissey, D. M., Finstad, C. L., Szkudlarek, J., Whitmore, W. F., Oettgen, H. F., Lloyd, K. O. and Old, L. J. Cell surface antigens of human renal cancer defin mouse monoclonal antibodies: Identification of tissue specific kidney glycoprcteins. Proc. Acad. Sci. 78:5122–5126 (1981).
Houghton, A. N., Eisinger, M. Albino, A. P., Cairncross, J. G. and Old, L. J. Surface antige melanocytes and melanomas. Markers of melanocyte differentiation and melanoma subsets.

Legend to TABLE IA
Serological Reaction of monoclonal antibodies of Ueda et al supra (*) and F23 mAb with tumor cell lines and normal cell lines.
0 = no reaction either by absorption or rosette formation
1 = reaction by absorption only
2 = reaction by rosette formation titer less than 10,000
3 = reaction by rosette formation titer greater than 10,000
4 = no reaction - only absorption test done
5 = reaction with absorption test only

TABLE IB
Serological characterization of seven prototype mouse Abs detecting surface antigens on human renal cancer cells

| Cells | Ab S$_4$ | | Ab S$_{24}$ | | Ab S$_{23}$ | | Ab S$_6$* | | Ab S$_{22}$ | | Ab V$_1$ | | Ab S$_{21}$ | |
|---|---|---|---|---|---|---|---|---|---|---|---|---|---|---|
|  | Titer ×10$^{-3}$ | Abs. | Titer ×10$^{-3}$ | Abs. | Titer ×10$^{-3}$ | Abs. | Titer ×10$^{-3}$ | Abs. | Titer ×10$^{-3}$ | Abs. | Titer ×10$^{-3}$ | Abs. | Titer ×10$^{-3}$ | Abs. |
| Epithelial cancers: |  |  |  |  |  |  |  |  |  |  |  |  |  |  |
| Renal |  |  |  |  |  |  |  |  |  |  |  |  |  |  |

TABLE IB-continued

Serological characterization of seven prototype mouse Abs detecting surface antigens on human renal cancer cells

| Cells | Ab S$_4$ Titer ×10$^{-3}$ | Abs. | Ab S$_{24}$ Titer ×10$^{-3}$ | Abs. | Ab S$_{23}$ Titer ×10$^{-3}$ | Abs. | Ab S$_6$* Titer ×10$^{-3}$ | Abs. | Ab S$_{22}$ Titer ×10$^{-3}$ | Abs. | Ab V$_1$ Titer ×10$^{-3}$ | Abs. | Ab S$_{21}$ Titer ×10$^{-3}$ | Abs. |
|---|---|---|---|---|---|---|---|---|---|---|---|---|---|---|
| SK-RC-1 (AA) | 50 | + | — | + | 1 | + | 50 | + | — | + | 500 | + | 50000 | + |
| SK-RC-2 (AB) | — | — | — | — | — | — | 50 | + | — | + | 500 | + | 5000 | + |
| SK-RC-4 (AE) | 50 | + | 500 | + | 50 | + | 50 | + | 5000 | + | 10000 | + | 5000 | + |
| SK-RC-6 (AG) | 50 | + | — | — | 10 | | 1000 | + | 5 | + | 10000 | + | 100000 | + |
| SK-RC-7 (AX) | 50 | + | 500 | + | 1 | + | 500 | + | 10000 | + | 10000 | + | 50000 | + |
| SK-RC-8 (BE) | — | — | 1 | + | 1 | + | 50 | + | 50 | + | 50 | + | 500 | + |
| SK-RC-9 (BM) | — | — | — | + | — | + | 500 | + | 50 | + | 5000 | + | 50000 | + |
| SK-RC-11 (BZ) | 5 | + | — | + | 1 | + | 1000 | + | — | + | 10000 | + | 50000 | + |
| SK-RC-21 (EB) | — | — | — | — | — | — | 500 | + | — | + | 1 | + | 50000 | + |
| SK-RC-28 (EU) | 50 | + | — | + | 500 | + | 5000 | + | — | + | 500 | + | 100000 | + |
| SK-RC-29 (BW) | — | — | — | — | — | — | 50 | + | — | + | 5000 | + | 50000 | + |
| A-498 | 10 | + | — | — | — | — | 50 | + | — | + | 10000 | + | 100 | + |
| CaKi-1 | — | — | — | — | — | — | 50 | + | — | + | 10000 | + | 100 | + |
| Bladder | | | | | | | | | | | | | | |
| RT-4 | — | — | — | — | — | — | — | — | — | + | 5000 | + | 50 | + |
| 5637 | — | — | — | — | — | — | — | — | — | + | — | — | 10 | + |
| T-24 | — | — | — | — | — | — | 5 | + | — | + | — | — | 10000 | + |
| 253J | — | — | — | — | — | — | 5 | + | — | + | 5000 | + | 5000 | + |
| Breast | | | | | | | | | | | | | | |
| AlAb | — | — | — | — | — | — | — | — | — | — | 5 | + | 500 | + |
| BT-20 | — | — | — | — | — | — | — | — | — | — | — | — | 50 | + |
| MCF-7 | — | — | — | — | — | — | — | — | — | — | 10000 | + | 1000 | + |
| SK-BR-3 | — | — | — | — | — | — | — | — | — | — | 10000 | + | 10 | + |
| Cervix | | | | | | | | | | | | | | |
| ME-180 | — | — | — | — | — | — | — | — | — | — | — | + | — | + |
| Colon | | | | | | | | | | | | | | |
| HT-29 | — | — | — | — | — | — | — | + | — | — | — | + | 50 | + |
| SW-1222 | — | — | — | — | — | — | — | — | — | — | 500 | + | 5 | + |
| Lung | | | | | | | | | | | | | | |
| SK-LC-LL | — | — | — | — | — | — | — | — | — | + | 1 | + | 5 | + |
| SK-LC-6 | — | — | — | — | — | — | 50 | + | — | — | 10000 | + | 50000 | + |
| Ovary | | | | | | | | | | | | | | |
| SK-OV-3 | — | — | — | — | — | — | — | — | 0.5 | + | — | + | 50 | + |
| Testicular | | | | | | | | | | | | | | |
| SK-GR-1 | — | — | — | — | — | — | — | — | — | — | — | + | 1 | + |
| Astrocytomas: | | | | | | | | | | | | | | |
| AJ, AS, BE | — | — | — | — | — | — | 5 | + | — | + | — | — | 500 | + |
| Melanomas: | | | | | | | | | | | | | | |
| SK-MEL-13, 28, 29, 37, 41 | — | — | — | — | — | — | — | — | — | — | 5000 | + | 5000 | + |
| SK-MEL-19 | — | — | — | — | — | — | — | — | — | — | 5000 | + | — | + |
| Neuroblastomas: | | | | | | | | | | | | | | |
| SK-NMC, SK-NSH | — | — | — | — | — | — | — | — | — | — | 1 | + | 100 | + |
| Lymphoblastoid cells: | | | | | | | | | | | | | | |
| EBV B cells AX, BE, EU | | — | | — | | — | | — | | — | | + | | + |
| Burkitt's lymphomas Raji, Daudi | | — | | — | | — | | — | | — | | + | | + |
| T cells MOLT-4, T-45 | | — | | — | | — | | — | | — | | | | + |
| Normal human cells | | | | | | | | | | | | | | |
| Kidney epithelium | | | | | | | | | | | | | | |
| ID | | — | | — | 10 | + | 5 | + | 1 | + | 5 | + | 25 | + |
| EQ, HY | 10 | + | — | — | 1.5 | + | 5 | + | 1 | + | 5 | + | 25 | + |
| GM, FR | 3 | + | 3 | + | 3 | + | 5 | + | 1 | + | 5 | + | 25 | + |
| EI, IJ | 3 | + | — | + | 1.5 | + | 5 | + | 1 | + | 5 | + | 25 | + |
| EG, GR, IB | 0.5 | + | — | — | 0.5 | + | 5 | + | 1 | + | 5 | + | 25 | + |
| Fetal kidney | | | | | | | | | | | | | | |
| C-4, C-8 | 0.5 | + | 2 | + | — | — | >5 | + | >5 | + | >5 | + | >5 | + |
| C-6 | — | — | 2 | + | — | — | >5 | + | >5 | + | >5 | + | >5 | + |
| Adult skin fibroblasts | — | — | — | — | — | — | 5 | + | — | — | — | — | 5 | + |
| Fetal lung fibroblasts | — | — | — | — | — | — | 1.5 | + | 0.5 | + | 0.5 | + | 10 | + |
| Fetal brain | — | — | — | — | — | — | — | | | + | — | — | 10 | + |
| Erthrocytes | — | | — | | — | | — | | — | | — | | — | |
| Xenogeneic cells: | | | | | | | | | | | | | | |
| Monkey kidney VERO | — | — | — | — | — | — | 5 | + | — | — | — | — | — | — |
| Sheep erythrocytes | | — | | — | | — | | — | | — | | — | | — |

Under "Titer," — indicates no reaction in direct tests at a dilution of 1:200. Abs., absorption tests. Sera (diluted to end point) were absorbed with the indicated cell type and tested for residual activity for SK-RC-7 (Ab S$_4$, Ab S$_6$, Ab S$_{23}$, Ab S$_{21}$), SK-RC-4 (Ab S$_{25}$), SK-RC-6 (Ab V$_1$), or SK-RC-28 (Ab S$_{23}$) target cells; +, complete absorption; —, no absorption. *mAb S$_{27}$ is derived from SK-RC-7 and has essentially the reactivity of mAb S$_6$.

TABLE II

TISSUE DISTRIBUTION OF THE MONOCLONAL ANTIBODIES OF THE KIDNEY

| | S4 | S6/27 | S23 | F23 | S22 | Q14 | AJ8 | NL-1 | NL-22 | P170 140 | C26 | C68 |
|---|---|---|---|---|---|---|---|---|---|---|---|---|
| A. FETAL TISSUES (NORMAL) | | | | | | | | | | | | |
| LUNG | 0 | 0 | 0 | 0 | 0 | 0 | 0 | 0 | 0 | 0 | + | 0 |
| Bronchial Epithelium | 0 | 0 | 0 | 0 | 0 | 0 | 0 | 0 | 0 | 0 | + | 0 |
| Cartilage | 0 | 0 | 0 | 0 | 0 | 0 | 0 | 0 | 0 | 0 | 0 | 0 |
| Pneumocytes | 0 | 0 | 0 | 0 | 0 | 0 | 0 | 0 | 0 | 0 | 0 | 0 |
| Connect. Tis | 0 | 0 | 0 | 0 | 0 | 0 | 0 | 0 | 0 | 0 | 0 | 0 |
| HEART | 0 | 0 | 0 | 0 | 0 | 0 | 0 | 0 | 0 | 0 | 0 | 0 |
| THYMUS | 0 | 0 | 0 | 0 | 0 | 0 | 0 | 0 | 0 | 0 | 0 | + |
| Hassal's C. | 0 | 0 | 0 | 0 | 0 | 0 | 0 | 0 | 0 | 0 | 0 | + |
| Thymocytes | 0 | 0 | 0 | 0 | 0 | 0 | 0 | 0 | 0 | 0 | 0 | 0 |
| SPLEEN | 0 | 0 | 0 | 0 | 0 | 0 | 0 | 0 | 0 | 0 | 0 | 0 |
| White Pulp | 0 | 0 | 0 | 0 | 0 | 0 | 0 | 0 | 0 | 0 | 0 | 0 |
| Red Pulp | 0 | 0 | 0 | 0 | 0 | 0 | 0 | 0 | 0 | 0 | 0 | 0 |
| LIVER | 0 | 0 | 0 | 0 | 0 | 0 | 0 | 0 | 0 | 0 | + | + |
| Hepatocytes | 0 | 0 | 0 | 0 | 0 | 0 | 0 | 0 | 0 | 0 | 0 | 0 |
| Biliary Epi. Cells | 0 | 0 | 0 | 0 | 0 | 0 | 0 | 0 | 0 | 0 | + | + |
| GALLBLAD. | 0 | 0 | 0 | 0 | 0 | 0 | 0 | 0 | 0 | 0 | + | + |
| ESOPHAGUS | 0 | 0 | 0 | 0 | 0 | 0 | 0 | 0 | 0 | 0 | ± | ± |
| STOMACH | 0 | 0 | 0 | 0 | 0 | 0 | 0 | 0 | 0 | 0 | 0 | + |
| SMALL INT. | 0 | 0 | 0 | 0 | 0 | 0 | 0 | 0 | 0 | 0 | ± | + |
| COLON | 0 | 0 | 0 | 0 | 0 | 0 | 0 | 0 | 0 | 0 | + | + |
| PANCREAS | 0 | 0 | 0 | 0 | 0 | 0 | 0 | 0 | 0 | 0 | + | 0 |
| Exocrine | 0 | 0 | 0 | 0 | 0 | 0 | 0 | 0 | 0 | 0 | + | 0 |
| Endocrine | 0 | 0 | 0 | 0 | 0 | 0 | 0 | 0 | 0 | 0 | 0 | 0 |
| KIDNEY | + | + | + | + | 0 | + | + | + | 0 | + | + | 0 |
| Glomerulus | + | 0 | 0 | 0 | 0 | + | + | + | 0 | + | 0 | 0 |
| Prox. Tub. | + | + | + | + | 0 | 0 | + | + | 0 | 0 | 0 | 0 |
| Distal Tub. | 0 | 0 | 0 | 0 | 0 | 0 | 0 | 0 | 0 | 0 | + | 0 |
| Collec. Tub. | 0 | 0 | 0 | 0 | 0 | 0 | 0 | 0 | 0 | 0 | + | 0 |
| URETER | 0 | + | 0 | 0 | 0 | 0 | 0 | 0 | 0 | 0 | + | + |
| UR. BLAD. | 0 | + | 0 | 0 | 0 | 0 | 0 | 0 | 0 | 0 | + | + |
| ADRENAL | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 |
| TESTES | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 |
| Endoc. Cel. | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 |
| OVARY | 0 | 0 | 0 | 0 | 0 | 0 | 0 | 0 | 0 | 0 | 0 | 0 |
| Germ. Cells | 0 | 0 | 0 | 0 | 0 | 0 | 0 | 0 | 0 | 0 | 0 | 0 |
| Connect. T. | 0 | 0 | 0 | 0 | 0 | 0 | 0 | 0 | 0 | 0 | 0 | 0 |
| FALLOP. T. | 0 | 0 | 0 | 0 | 0 | 0 | 0 | 0 | 0 | 0 | + | 0 |
| UTERUS | 0 | 0 | 0 | 0 | 0 | 0 | 0 | 0 | 0 | 0 | + | 0 |
| Endometrium | 0 | 0 | 0 | 0 | 0 | 0 | 0 | 0 | 0 | 0 | + | 0 |
| Myometrium | + | 0 | 0 | 0 | 0 | 0 | 0 | 0 | 0 | 0 | 0 | 0 |
| CERVIX | 0 | 0 | 0 | 0 | 0 | 0 | 0 | 0 | 0 | 0 | + | + |
| Endocervix | 0 | 0 | 0 | 0 | 0 | 0 | 0 | 0 | 0 | 0 | + | 0 |
| Exocervix | 0 | 0 | 0 | 0 | 0 | 0 | 0 | 0 | 0 | 0 | 0 | + |
| SKIN | 0 | 0 | 0 | 0 | 0 | 0 | 0 | 0 | 0 | 0 | + | + |
| Epidermas | 0 | 0 | 0 | 0 | 0 | 0 | 0 | 0 | 0 | 0 | ± | ± |
| Melanocytes | 0 | 0 | 0 | 0 | 0 | 0 | 0 | 0 | 0 | 0 | 0 | 0 |
| Sweat Gland | 0 | 0 | 0 | 0 | 0 | 0 | 0 | 0 | 0 | 0 | + | 0 |
| Sebac. Gld. | 0 | 0 | 0 | 0 | 0 | 0 | 0 | 0 | 0 | 0 | 0 | 0 |
| Hair Fol. | 0 | 0 | 0 | 0 | 0 | 0 | 0 | 0 | 0 | 0 | 0 | 0 |
| Dermis C.T. | 0 | 0 | 0 | 0 | 0 | 0 | 0 | 0 | 0 | 0 | 0 | 0 |
| BRAIN | 0 | 0 | 0 | 0 | 0 | 0 | 0 | 0 | 0 | 0 | 0 | 0 |
| Neurons | 0 | 0 | 0 | 0 | 0 | 0 | 0 | 0 | 0 | 0 | 0 | 0 |
| Glial Cells | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 |
| BLOOD VES. | + | 0 | 0 | 0 | 0 | + | 0 | 0 | 0 | 0 | 0 | 0 |
| Endoth. Cel. | 0 | 0 | 0 | 0 | 0 | + | 0 | 0 | 0 | 0 | 0 | 0 |
| Smooth Ms. | + | 0 | 0 | 0 | 0 | 0 | 0 | 0 | 0 | 0 | 0 | 0 |
| SOFT TIS. | 0 | 0 | 0 | 0 | 0 | 0 | + | 0 | 0 | + | 0 | 0 |
| SECRETION | 0 | 0 | 0 | 0 | 0 | 0 | 0 | 0 | 0 | 0 | + | + |
| B. ADULT TISSUES (Normal) | | | | | | | | | | | | |
| LUNG | 0 | 0 | 0 | 0 | 0 | 0 | 0 | 0 | 0 | 0 | + | 0 |
| Bronchial Epithelium | 0 | 0 | 0 | 0 | 0 | 0 | 0 | 0 | 0 | 0 | + | 0 |
| Cartilage | 0 | 0 | 0 | 0 | 0 | 0 | 0 | 0 | 0 | 0 | 0 | 0 |
| Glandular Epithelium | 0 | 0 | 0 | 0 | 0 | 0 | 0 | 0 | 0 | 0 | + | 0 |
| Pneumocytes | 0 | 0 | 0 | 0 | 0 | 0 | 0 | 0 | 0 | 0 | 0 | 0 |
| Connect. Tis. | 0 | 0 | 0 | 0 | 0 | 0 | 0 | 0 | 0 | 0 | 0 | 0 |
| HEART (ms) | 0 | 0 | 0 | 0 | 0 | 0 | 0 | 0 | 0 | 0 | 0 | 0 |

TABLE II-continued
TISSUE DISTRIBUTION OF THE MONOCLONAL ANTIBODIES OF THE KIDNEY

| | | | | | | | | | | | | |
|---|---|---|---|---|---|---|---|---|---|---|---|---|
| SPLEEN | 0 | 0 | 0 | 0 | 0 | 0 | 0 | 0 | 0 | 0 | 0 | 0 |
| White pulp | 0 | 0 | 0 | 0 | 0 | 0 | 0 | 0 | 0 | 0 | 0 | 0 |
| Red pulp | 0 | 0 | 0 | 0 | 0 | 0 | 0 | 0 | 0 | 0 | 0 | 0 |
| LIVER | 0 | 0 | 0 | 0 | 0 | 0 | 0 | 0 | 0 | 0 | + | 0 |
| Hepatocyte | 0 | 0 | 0 | 0 | 0 | 0 | 0 | 0 | 0 | 0 | 0 | 0 |
| Bil. Epit. | 0 | 0 | 0 | 0 | 0 | 0 | 0 | 0 | 0 | 0 | + | 0 |
| Sinusoids | 0 | 0 | 0 | 0 | 0 | 0 | 0 | 0 | 0 | 0 | 0 | 0 |
| GALLBLADDER | 0 | 0 | 0 | 0 | 0 | 0 | 0 | 0 | 0 | 0 | + | 0 |
| ESOPHAGUS | 0 | 0 | 0 | 0 | 0 | 0 | 0 | 0 | 0 | 0 | 0 | 0 |
| STOMACH | 0 | 0 | 0 | 0 | 0 | 0 | 0 | 0 | 0 | 0 | 0 | + |
| SM. INTEST. | 0 | 0 | 0 | 0 | 0 | 0 | 0 | 0 | 0 | 0 | 0 | + |
| COLON | 0 | + | + | 0 | 0 | 0 | 0 | 0 | 0 | 0 | + | + |
| G.I. Smc. | 0 | 0 | 0 | 0 | 0 | 0 | 0 | 0 | 0 | 0 | 0 | 0 |
| PANCREAS | 0 | 0 | 0 | 0 | 0 | 0 | 0 | 0 | 0 | 0 | + | 0 |
| Exocrine | 0 | 0 | 0 | 0 | 0 | 0 | 0 | 0 | 0 | 0 | + | 0 |
| Endocrine | 0 | 0 | 0 | 0 | 0 | 0 | 0 | 0 | 0 | 0 | 0 | 0 |
| KIDNEY | + | + | + | + | 0 | + | + | + | + | + | + | 0 |
| Glomerulus | + | 0 | 0 | 0 | 0 | + | + | + | 0 | + | 0 | 0 |
| Prox. Tub. | + | + | + | + | 0 | 0 | + | + | + | 0 | 0 | 0 |
| Henle's L. | 0 | ± | 0 | 0 | 0 | 0 | ± | 0 | 0 | 0 | ± | 0 |
| Distal Tub. | 0 | 0 | 0 | 0 | 0 | 0 | 0 | 0 | 0 | 0 | + | 0 |
| Collec. Tub. | 0 | 0 | 0 | 0 | 0 | 0 | 0 | 0 | 0 | 0 | + | 0 |
| URETER | 0 | + | 0 | 0 | 0 | 0 | 0 | 0 | 0 | 0 | + | + |
| URI. BLAD. | 0 | + | 0 | 0 | 0 | 0 | 0 | 0 | 0 | 0 | + | + |
| ADRENAL | 0 | 0 | 0 | 0 | 0 | 0 | 0 | 0 | 0 | 0 | 0 | 0 |
| Cortex | 0 | 0 | 0 | 0 | 0 | 0 | 0 | 0 | 0 | 0 | 0 | 0 |
| Medulla | 0 | 0 | 0 | 0 | 0 | 0 | 0 | 0 | 0 | 0 | 0 | 0 |
| THYROID | 0 | 0 | 0 | 0 | 0 | 0 | 0 | 0 | 0 | 0 | 0 | 0 |
| Epithelium | 0 | 0 | 0 | 0 | 0 | 0 | 0 | 0 | 0 | 0 | 0 | 0 |
| Colloid | 0 | 0 | 0 | 0 | 0 | 0 | 0 | 0 | 0 | 0 | 0 | 0 |
| BREAST | 0 | 0 | 0 | 0 | 0 | 0 | 0 | 0 | 0 | 0 | + | + |
| Duct Cells | 0 | 0 | 0 | 0 | 0 | 0 | 0 | 0 | 0 | 0 | + | + |
| Acinar Cel. | 0 | 0 | 0 | 0 | 0 | 0 | 0 | 0 | 0 | 0 | + | 0 |
| Connec. Tis. | 0 | 0 | 0 | 0 | 0 | 0 | 0 | 0 | 0 | 0 | 0 | 0 |
| PROSTATE | 0 | + | + | 0 | 0 | 0 | 0 | 0 | 0 | 0 | + | + |
| Epithelium | 0 | + | + | 0 | 0 | 0 | 0 | 0 | 0 | 0 | + | + |
| Stroma | 0 | 0 | 0 | 0 | 0 | 0 | 0 | 0 | 0 | 0 | 0 | 0 |
| TESTE | 0 | 0 | 0 | 0 | 0 | 0 | 0 | 0 | 0 | 0 | 0 | 0 |
| Germ Cells | 0 | 0 | 0 | 0 | 0 | 0 | 0 | 0 | 0 | 0 | 0 | 0 |
| Endocrine Cells | 0 | 0 | 0 | 0 | 0 | 0 | 0 | 0 | 0 | 0 | 0 | 0 |
| Connec. Tis. | 0 | 0 | 0 | 0 | 0 | 0 | 0 | 0 | 0 | 0 | 0 | 0 |
| FALLOP. TUB. | 0 | 0 | 0 | 0 | 0 | 0 | 0 | 0 | 0 | 0 | 0 | 0 |
| UTERUS | 0 | 0 | 0 | 0 | 0 | 0 | 0 | 0 | 0 | 0 | + | 0 |
| Endometrium | 0 | 0 | 0 | 0 | 0 | 0 | 0 | 0 | 0 | 0 | + | 0 |
| Myometrium | + | 0 | 0 | 0 | 0 | 0 | 0 | 0 | 0 | 0 | 0 | 0 |
| CERVIX | 0 | 0 | 0 | 0 | 0 | 0 | 0 | 0 | 0 | 0 | + | + |
| Endocervix | 0 | 0 | 0 | 0 | 0 | 0 | 0 | 0 | 0 | 0 | + | 0 |
| Exoceruix | 0 | 0 | 0 | 0 | 0 | 0 | 0 | 0 | 0 | 0 | + | + |
| PLACENTA | 0 | 0 | 0 | 0 | 0 | 0 | 0 | 0 | 0 | 0 | 0 | 0 |
| Cytotrophb. | 0 | 0 | 0 | 0 | 0 | 0 | 0 | 0 | 0 | 0 | 0 | 0 |
| Syncytotrb. | 0 | 0 | 0 | 0 | 0 | 0 | 0 | 0 | 0 | 0 | 0 | 0 |
| Sinusoids | 0 | 0 | 0 | 0 | 0 | 0 | 0 | 0 | 0 | 0 | 0 | 0 |
| SKIN | 0 | 0 | 0 | 0 | 0 | 0 | 0 | 0 | 0 | 0 | + | 0 |
| Epidermis | 0 | 0 | 0 | 0 | 0 | 0 | 0 | 0 | 0 | 0 | + | 0 |
| Melanocytes | 0 | 0 | 0 | 0 | 0 | 0 | 0 | 0 | 0 | 0 | 0 | 0 |
| Sweat Gld. | 0 | 0 | 0 | 0 | 0 | 0 | 0 | 0 | 0 | 0 | + | 0 |
| Sebaceous G. | 0 | 0 | 0 | 0 | 0 | 0 | 0 | 0 | 0 | 0 | + | 0 |
| Dermis CT | 0 | 0 | 0 | 0 | 0 | 0 | 0 | 0 | 0 | 0 | 0 | 0 |
| BRAIN | 0 | 0 | 0 | 0 | 0 | 0 | + | 0 | 0 | + | 0 | 0 |
| Neurons | 0 | 0 | 0 | 0 | 0 | 0 | ± | 0 | 0 | ± | 0 | 0 |
| Glial Cell | 0 | 0 | 0 | 0 | 0 | 0 | 0 | 0 | 0 | 0 | 0 | 0 |
| Dendrites | 0 | 0 | 0 | 0 | 0 | 0 | 0 | 0 | 0 | 0 | 0 | 0 |
| LYMPH NODE | 0 | 0 | 0 | 0 | 0 | 0 | 0 | 0 | 0 | 0 | 0 | 0 |
| Fol/Medul | 0 | 0 | 0 | 0 | 0 | 0 | 0 | 0 | 0 | 0 | 0 | 0 |
| BLOOD VES. | + | 0 | 0 | 0 | 0 | + | 0 | 0 | 0 | 0 | 0 | 0 |
| Endothelium | 0 | 0 | 0 | 0 | 0 | + | 0 | 0 | 0 | 0 | + | + |
| Smooth Ms. | + | 0 | 0 | 0 | 0 | 0 | 0 | 0 | 0 | 0 | 0 | 0 |
| CAPILLARIES | 0 | 0 | 0 | 0 | 0 | + | 0 | 0 | 0 | 0 | 0 | 0 |
| SKELETAL MS | 0 | 0 | 0 | 0 | 0 | 0 | 0 | 0 | 0 | 0 | 0 | 0 |
| SOFT TISSUE | 0 | 0 | 0 | + | 0 | 0 | 0 | 0 | 0 | 0 | + | 0 |
| SECRETIONS | 0 | 0 | 0 | 0 | 0 | 0 | 0 | 0 | 0 | 0 | + | + |
| | S6 | S4 | F23 | S23 | S22 | S25 | S27 | C26 | T43 | T16 | T87 | |

C. RENAL CARCINOMAS

| | S6 | S4 | F23 | S23 | S22 | S25 | S27 | C26 | T43 | T16 | T87 |
|---|---|---|---|---|---|---|---|---|---|---|---|
| RC #3 | + | + | + | 0 | 0 | 0 | | 0 | + | 0 | 0 |
| RC #5 | + | ± | ± | ± | 0 | 0 | ± | ± | ± | ± | |
| RC #6 | + | + | + | + | ± | 0 | 0 | ± | 0 | 0 | |
| RC #2 | + | + | ± | + | 0 | 0 | ± | 0 | 0 | ± | |
| RC #7 | + | + | ± | + | 0 | 0 | 0 | ± | 0 | 0 | |

TABLE II-continued
TISSUE DISTRIBUTION OF THE MONOCLONAL ANTIBODIES OF THE KIDNEY

| | | | | | | | | | | | | |
|---|---|---|---|---|---|---|---|---|---|---|---|---|
| RC #9 | + | ± | 0 | + | 0 | 0 | 0 | 0 | 0 | 0 | | |
| RC #10 | + | 0 | 0 | + | ± | 0 | + | 0 | + | + | | |
| RC #11 | + | + | ± | 0 | ± | 0 | ± | 0 | 0 | 0 | | |
| RC #12 | + | + | + | 0 | 0 | 0 | | 0 | 0 | 0 | 0 | |
| RC #13 | + | + | + | 0 | 0 | 0 | | 0 | 0 | 0 | 0 | |
| RC #22 | + | 0 | ± | 0 | 0 | 0 | | ± | + | 0 | + | |
| RC #23 | + | + | + | + | 0 | 0 | | 0 | + | 0 | 0 | |
| RC #14 | + | ± | 0 | 0 | 0 | 0 | | 0 | 0 | 0 | 0 | |
| RC #16 | + | + | ± | ± | 0 | | | 0 | 0 | 0 | 0 | |
| RC #19 | + | + | ± | + | 0 | | + | 0 | + | 0 | 0 | |
| RC #18 | + | 0 | 0 | 0 | 0 | | | | 0 | + | + | |
| RC #21 | + | + | ± | + | ± | | + | 0 | 0 | | | |
| RC #15 | + | 0 | 0 | 0 | 0 | | 0 | ± | + | | | |
| Billoti (NSUH) | + | 0 | 0 | ± | 0 | | + | 0 | ± | 0 | 0 | |
| Pipet (NYU) | + | ± | ± | + | ± | | + | 0 | 0 | 0 | 0 | |
| RC #17 | + | ± | ± | ± | ± | | + | ± | | ± | ± | |
| RC #20 | + | ± | ± | + | ± | | + | 0 | | 0 | 0 | |
| RC #24 | + | 0 | ± | ± | ± | | ± | 0 | | 0 | | |
| RC #25 | 0 | 0 | 0 | 0 | 0 | | 0 | 0 | 0 | 0 | 0 | |

| | Melan. N9 | S4 | S22 | F23 | S23 | S27 | S25 | V1 | C26 | T16 | AJ8 | NL-1 |
|---|---|---|---|---|---|---|---|---|---|---|---|---|
| D. Summary of tumor immunopathology staining using FITC-rabbit anti-mouse IgG | | | | | | | | | | | | |
| Colon | | | | | | | | | | | | |
| 82-18240 | 0 | 0 | 0 | 0 | + | 0 | + | 0 | + | 0 | 0 | 0 |
| 83-153 | 0 | 0 | 0 | 0 | + | 0 | + | 0 | + | 0 | 0 | 0 |
| 82-16115 | 0 | 0 | 0 | 0 | + | 0 | + | 0 | + | 0 | 0 | 0 |
| 82-21302 | 0 | 0 | 0 | 0 | 0 | 0 | + | 0 | + | 0 | 0 | 0 |
| invad. adenoca | 0 | 0 | 0 | 0 | 0 | 0 | + | 0 | + | 0 | 0 | 0 |
| Lung | | | | | | | | | | | | |
| 83-692 | 0 | 0 | 0 | 0 | 0 | 0 | + | 0 | + | 0 | 0 | 0 |
| 83-2016 | 0 | 0 | 0 | + | ± | 0 | + | 0 | + | + | 0 | 0 |
| 83-323 | 0 | 0 | 0 | 0 | 0 | 0 | + | 0 | 0 | 0 | 0 | 0 |
| 83-337 | 0 | 0 | 0 | 0 | 0 | 0 | + | 0 | + | + | 0 | 0 |
| Oat cell ca | 0 | 0 | 0 | 0 | 0 | 0 | + | 0 | + | 0 | 0 | 0 |
| Breast | | | | | | | | | | | | |
| fibroadenoma | 0 | 0 | 0 | ± | 0 | 0 | 0 | 0 | + | 0 | 0 | 0 |
| 82-15096 | 0 | 0 | 0 | + | 0 | 0 | + | 0 | + | + | 0 | 0 |
| 82-7783 | 0 | 0 | 0 | 0 | 0 | 0 | + | + | + | 0 | 0 | |
| 82-14627 | 0 | 0 | 0 | 0 | 0 | 0 | + | 0 | + | + | 0 | 0 |
| met to lym. n. | 0 | 0 | 0 | 0 | 0 | 0 | + | 0 | + | 0 | 0 | 0 |
| Bladder | | | | | | | | | | | | |
| papilloma | 0 | 0 | 0 | 0 | 0 | 0 | + | 0 | + | + | 0 | 0 |
| Arnold/in situ | 0 | 0 | 0 | 0 | 0 | 0 | 0 | 0 | 0 | + | 0 | 0 |
| Grant TCC | 0 | 0 | 0 | 0 | 0 | 0 | 0 | 0 | 0 | + | 0 | 0 |
| Wilson TCC | 0 | 0 | 0 | 0 | 0 | 0 | + | 0 | + | + | 0 | 0 |
| Caurin TCC | 0 | 0 | ± | 0 | 0 | 0 | + | 0 | + | + | 0 | 0 |
| Ureter Teratoca | | | | | | | | | | | | |
| 82-20793 | 0 | 0 | 0 | + | + | + | 0 | 0 | 0 | + | + | + |
| 83-1881a | 0 | 0 | 0 | 0 | 0 | 0 | + | 0 | + | 0 | 0 | 0 |
| 83-1881b | 0 | 0 | 0 | 0 | 0 | 0 | + | 0 | 0 | 0 | 0 | 0 |
| 82-19590 | 0 | 0 | 0 | 0 | 0 | 0 | + | 0 | + | 0 | 0 | 0 |
| 82-23735 | 0 | 0 | 0 | + | 0 | 0 | + | 0 | 0 | 0 | 0 | 0 |
| Nevus Melanosarc. | | | | | | | | | | | | |
| 82-16834 | + | 0 | 0 | + | 0 | 0 | + | 0 | 0 | 0 | 0 | 0 |
| Astrocytoma | | | | | | | | | | | | |
| grade I | 0 | 0 | 0 | + | 0 | 0 | 0 | 0 | 0 | 0 | 0 | 0 |
| grade III | 0 | 0 | 0 | 0 | 0 | 0 | 0 | 0 | 0 | 0 | 0 | 0 |
| Lymphoma | | | | | | | | | | | | |
| 82-16027 | 0 | 0 | 0 | 0 | 0 | 0 | 0 | 0 | 0 | 0 | 0 | 0 |
| 83-2542 | 0 | 0 | 0 | 0 | 0 | 0 | + | 0 | 0 | 0 | 0 | 0 |
| smooth muscle | + | 0 | 0 | 0 | 0 | 0 | 0 | 0 | 0 | 0 | 0 | 0 |
| endothelial C. | + | 0 | 0 | 0 | 0 | 0 | 0 | 0 | 0 | 0 | 0 | 0 |
| interstitial | 0 | + | 0 | 0 | 0 | 0 | 0 | 0 | 0 | 0 | 0 | 0 |
| fibroblast | 0 | 0 | 0 | + | 0 | 0 | + | 0 | 0 | 0 | 0 | 0 |

TABLE II-continued
TISSUE DISTRIBUTION OF THE MONOCLONAL ANTIBODIES OF THE KIDNEY

| connect. tis. | 0 | 0 | 0 | + | 0 | 0 | + | 0 | 0 | 0 | 0 | 0 |

Legend to TABLE II
Immunopathological reaction of monoclonal antibodies of Ueda et al supra (*) and F23 mAb with frozen tumor or normal human tissue sections by immunofluorescence.
For parts A & B frozen sections of normal human tissue:
0 = no reaction
± = heterogeneous positive reaction within the tissue
+ = homogeneous positive reaction within the tissue
For parts C & D - frozen sections of human tumors
0 = no reaction
± = heterogeneous reaction
+ = positive reaction
Note:
C68 = colon monoclonal antibody CLH68 (co-pending application Serial No. 474,415)
C26 = colon monoclonal antibody HT29/26 (co-pending application supra)
AJ8 = astrocytoma monoclonal antibody (Cairncross, et al. Proc. Nat'l. Acad. Sci. U.S.A. 1982) co-pending serial number 413,861.
NL-1 = monoclonal antibody recognizing calla antigen in acute lymphocytic leukemia (Tanimoto)
NL-22 = mAb (Tanimoto)
Q-14 = melanoma antibody (co-pending application Serial #445,561)
P170 = AJ2 astrocytoma (Cairncross, Supra)
P130 = AJ2 astrocytoma (Cairncross, Supra)
$S_6/S_{27}$ refers to tests done using either $S_6$ or $S_{27}$ mAb which gives same reaction Antigenic Systems:

gp160 Antigenic System. Five Abs in this series ($S_4$, $S_7$, $S_{11}$, $S_{24}$, and $M_1$) identifies a 160,000-dalton glycoprotein that showed a high degree of specificity for human kidney cells. gp160 is a rather basic component with pI 7.5. By M-MHA tests, gp160 could be demonstrated on all cultures of normal kidney epithelium, 2 of 3 cultures of fetal kidney, and 7 of 13 established lines of renal cancer (Table 2). These results were confirmed in absorption tests. No other cell type, normal or malignant, was found to express the gp160 antigen, including VERO, a cell line derived from monkey kidney.

$S_{25}$ Antigenic System. The antigen detected by Ab $S_{25}$ also is restricted to human cells of renal origin (Table 2). The $S_{25}$ determinant is heat labile, suggesting that it resides on a protein or glucoprotein, but Ab $S_{25}$ did not precipitate any detectable component from [$^{35}$S] methionine-labeled or [$^3$H] glucosamine-labeled SK-RC-7 cells. Comparison of the $S_{25}$ and the gp160 phenotypes of different renal cancer lines and cultures of normal kidney clearly distinguished these two systems. For example, SK-RC-6 and A-498 are gp160+/$S_{25}$- and SK-RC-8 is gp160-/$S_{25}$+, whereas five of these cultures lacked $S_{25}$ expression.

gp120r and gp120nr Antigenic Systems. Five Abs ($S_{23}$, $S_{26}$, $S_{27}$, $S_6$, and $S_1$) immunoprecipitated a 120,000-dalton glycoprotein from [$^{35}$S] methionine- or [$^3$H] glucosamine-labeled lysates of SK-RC-7 cells. Analysis under reducing and nonreducing conditions gave the same results. The pIs of gp120 identified by prototype Ab $S_6$ and Ab $S_{23}$ were identical (4.9–5.2). A further indication of the relatedness of the gp120 components identified by these two groups of Abs came from sequential immunoprecipitation tests. Pretreatment of [$^3$H] glucosamine-labeled lysates of SK-RC-7 with Ab $S_6$ removed all antigen reactive with Ab $S_{23}$. In contrast, M-MHA tests and absorption analysis (Table 2) showed that these gp120 antibodies identified two serologically distinct gp120 epitopes that distinguish two classes of gp120 molecules: gp120r (restricted) and gp120nr (nonrestricted).

gp120r, identified by Ab $S_{23}$, had a highly restricted distribution, expression being limited to normal kidney epithelium and certain renal cancers. The other gp120 epitope, gp120nr, identified by Ab $S_6$ and Ab $S_{27}$, was found on a wide range of cultured cells including fetal and adult fibroblasts and cell lines derived from ovarian, bladder, and colon cancers. gp120r and gp120nr determinants differ in their expression on renal cancer cell lines: all cell lines carry the gp120nr epitope, whereas SK-RC-2, -21, -29, and Caki-1 lack gp120r determinants. The specificity of Ab $S_{23}$ for cells of renal origin resembles the reactivity of Ab $S_{25}$ and, most particularly, antibodies identifying the gp160 system. However, in addition to the molecular weight differences in the gp160 and gp120 antigens, these three kidney-specific antigenic systems can be distinguished on the basis of absorption analysis with selected normal or malignant kidney cells-e.g., SK-RC-6 and A-498 are are gp160+/$S_{25}$-/gp120r+; fetal kidney is gp160+ or -/$S_{25}$+/gp120r-.

gp115 Antigenic System. Ab $S_{22}$ immunoprecipitated a 115,000-dalton glycoprotein from [$^3$H] glucosamine- or [$^{35}$S] methionine-labeled lysates of SK-RC-7 cells under both reduced and nonreduced conditions. In direct M-MHA tests, high reactivity (titers, $1–10,000\times10^{-3}$) was restricted to certain renal cancer cells and normal kidney epithelium. Absorption analysis, however, revealed that the gp115 antigen was expressed by various cell types.

gp140 antigenic system

MAb F23 recognizes another antigenic system gp140. $F_{23}$, is a gamma sub 2A (gamma 2A) immunoglobulin (Ig) antibody. MAb $S_4$ was in that same class of Ig while $S_{25}$, $S_{22}$, $S_{23}$, $S_6$, $S_{27}$, $V_1$ and $S_{21}$ belonged to immunoglobulin class gamma sub one (gamma $_1$) and $M_2$ and $S_8$ to Ig class mu(u). $F_{23}$ recognizes a new antigenic system on human renal cells-glycoprotein (gp) 140.

$F_{23}$ is derived from a hybridoma cell line wherein normal human renal epithelial cells are the immunogen. Yet $F_{23}$ monoclonal antibody recognize renal tumor antigens. This was an unexpected result.

As can be seen from Table I, $F_{23}$ recognizes human renal cancer cell lines. Of 25 cell lines tested, $F_{23}$ is positive for 19 of those. 33 human renal cell lines were studied. $F_{23}$ also recognizes some poorly differentiated renal carcinomas and some renal carcinomas with papillary differentiation with its best reaction with well differentiated renal carcinomas i.e. $F_{23}$ subsets renal carcinomas and can be used to assay for the malignant potential of renal tumors. Frozen renal carcinoma sections for over 20 different human specimens were tested as well. Comparison of frozen sections and tissue culture lines established from the same specimens reveals that for most antigens, expression is consistent in vivo and in vitro. See tables I & II.

$F_{23}$ also gives a positive reaction with all cell lines of normal kidney epithelium. However, $F_{23}$ did not react with normal human A, B or O erythrocytes by the absorption test. In frozen sections, $F_{23}$ reacted with normal kidney and proximal tubule in fetal as well as adult specimens. Table II Some antigens may be either induced or suppressed in tissue culture. This characteristic must be determined for each antigen prior to extrapolating results between in vivo and in vitro systems.

Therefore $F_{23}$ mAb is added to the mAb panel for human renal cancer which to date includes then $F_{23}$, $M_1$, $M_2$, $S_1$, $S_4$, $S_6$, $S_7$, $S_8$, $S_{11}$, $S_{21}$, $S_{22}$, $S_{23}$, $S_{24}$, $S_{25}$, $S_{26}$, $S_{27}$, $V_1$ and $V_2$. This entire array of mAbs is used to diagnose renal cancer. To this panel must be added new mAb $F_{31}$ as well (see below). A specimen tissue, body waste or fluid or exudate is contacted separately with each of the mAbs in a screening test for a positive reaction. These mAbs are also useful in tissue typing—whether of normal or tumor tissue. $F_{23}$ is the invention relating to U.S. Pat. Ser. No. 474,224.

$V_1$ Antigenic System. Ab $V_1$ did not immunoprecipitate any labeled component from [$^3$H] glucosamine- or [$^{35}$S] methionine-labeled lysates of SK-RC-7 cells. Absorption tests indicated that the antigen is heat stable (5 mins. at 100° C.), suggesting that it is a glycolipid. Two features of the $V_1$ (Table 2) system are of particular interest: (a) it identifies a subset of bladder and breast cancers that do not express $V_1$, and (b) $V_1$ is not found on astrocytomas, whereas melanomas are strong $V_1$ expressors. This clear distinction between astrocytomas and melanoma, whose embryonic derivations are closely related, has not been seen with other Abs.

HLA Heavy Chain. Ab $S_{21}$ immunoprecipitated a 45,000- and a 12,000-dalton component from [$^{35}$S] methionine-labeled SK-RC-7 lysates. The determinant detected by Ab $S_{21}$ in direct and absorption tests was present on virtually every human cell type with the exception of human erythrocytes (Table I). Of all the human cultured cells tested, the only cell lines not reactive with Ab $S_{21}$ in direct MHA tests were ME-180 and SK-MEL-19; the SK-MEL-19 melanoma cell line is known from previous work to express little or no HLA—A, —B, —C antigens. The molecular weights of the components precipitated by Ab $S_{21}$ and the results of the serological survey of human cells-indicated that Ab $S_{21}$ detected HLA but did not distinguish between a determinant on the heavy chain or on the gamma $_2$m chain. The fact that isolated human gamma $_2$m did not inhibit the reactivity of Ab $S_{21}$ suggests specificity for HLA heavy chain.

A and B Blood Group Antigens. Renal cancer line used for immunization (Table I) expresses blood group B antigen on its cell surfaces i.e. SK-RC-7 is B+, while SK-RC-28 is A+. SK-RC-6 is derived from a type O individual and is negative for A and B reactivities. To detect Abs reacting with blood group antigens, hybridoma supernatants were screened for hemagglutinating antibody by using A, B, AB, or O erythrocytes. B (but not A) agglutinating activity was found in 4 of 462 supernatants from the anti-SK-RC-7 (fusion) and A (but not B) agglutinating activity was found in 3 of 225 supernatants from the anti-SK-RC-28 fusion. No agglutination of type O erythrocytes was found in supernatants from anti-SK-RC-7, -28 or -6 fusions. Two monoclonal antibodies with hemagglutinin activity were derived from these fusions. The hemagglutination titer of Ab $M_2$ (nu/nu serum) for A and AB erythrocytes was $10^{-4}$; B erythrocytes were not agglutinated by Ab $M_2$. The hemagglutination titler of Ab $S_8$ (nu/nu serum) for B and AB erythrocytes was $4 \times 10^{-5}$; A type erythrocytes were not agglutinated by Ab $S_8$.

MAb $F_{31}$

SK-RC-1 is the immunizing cell line producing the new monoclonal antibody $F_{31}$. Indications are that $F_{31}$ reacts with a glycoprotein antigen on renal cells. The specificity in tissue culture of $F_{31}$ is illustrated in Table III using the red cell rosette anti-mouse Ig assay using human red cells conjugated with rabbit-anti-mouse Ig as indicator of immunological reaction. Table III shows the titration endpoint of this reaction with RC cell lines and $F_{31}$ mAb. As can be seen $F_{31}$ is highly restricted to human renal carcinoma cell lines as opposed to cancer cell lines from other tissues.

Some normal kidney reacts with $F_{31}$. Immunochemistry shows $F_{31}$ to be an IgM antibody.

Frozen sections of normal kidney (NK) tissue done on seven NK samples shows $F_{31}$ reacting with the distal end of the proximal tubule of the kidney and early portion of Henle's loop. Frozen sections of RC show approximately 4/5 positive for mAb $F_{31}$.

In Table IV the distribution of antigens on the kidney nephron is illustrated. Since approximately 80% of RC appear to be F31+ these tumors probably arise from the area of overlap of reactivity $F_{31}$ with other antigens also expressed by RC.

The panel of mAb localizes the site where most RC probably arise. Therapy methods as described above should therefore probably be directed to this area. For example, mAb for this area or mixtures thereof can be used alone or combined with cytotoxic or cytostatic agents for therapy in renal carcinoma.

TABLE III

Specificity in Tissue Culture of mAb $F_{31}$

| Human Tumor: | Cell line | Titers 1/ |
|---|---|---|
| Kidney: | SK-RC-1 | 1000 |
| | 2 | 5000 |
| | 4 | — |
| | 6 | 1000 |
| | 7 | 1000 |
| | 9 | — |
| | 10 | 5000 |
| | 12 | — |
| | 15 | 25000 |
| | 17 | 25000 |
| | 18 | 1000 |
| | 20 | 5000 |
| | 21 | — |
| | 24 | — |
| | 26A | 1000 |
| | 26B | — |
| | 28 | 5000 |
| | 29 | 5000 |
| | 31 | 5000 |
| | 33 | 5000 |
| | 34 | 25000 |
| | 35 | 5000 |
| | 37 | 1000 |
| | 38 | 25000 |
| | 39 | 5000 |
| | 40 | 5000 |
| | " | 5000 |
| | 42 | 5000 |
| | 44 | 25000 |
| | 45 | 5000 |
| | 46 | 5000 |
| | 47 | — |

TABLE III-continued
Specificity in Tissue Culture of mAb F$_{31}$

| Human Tumor: | Cell line | Titers 1/ |
|---|---|---|
| | 48 | 5000 |
| | 49 | 25000 |
| | 50 | 125000 |
| | 51 | — |

(— indicates negative)
Rosette-assay: Human o red cells conjugated with rabbit anti-mouse Ig. For anti-IgG assays (IgG-MHA) indicator cells were prepared by conjugating the immunoglobulin fraction of rabbit anti-mouse Ig (DAKO, Copenhagen) to human O erythrocytes with 0.01% chromium chloride.

Cell line: (Human)

Bladder - all negative
| 2535 | 5637 | 575A | UM-CUB-3 |
| UM CUB-1 | SCABER | JON | |
| T-24 | SW780 | VM CUB-2 | |

Breast - all negative
| MCF-7 | BT-20 | CAMA | |
| MDA-MB-231 | ALAB | | |

Prostate - all negative
| DU 145 | PC3 | LNCAP | |

Colon - all negative
| HT29 | Tallevi | Redmond | SW1222 |

Pancreas - all negative
| CAPAN-2 | ASPC-1 | CAPAN-1 | |

Ovarian - all negative
| Shustach | SW626 | Turaneck | |

Cervix - negative
ME-180
Lung - 25 line negative
SK-LC number 1 through 20
*Melanoma - 8 lines negative
*Astrocytoma 4 lines negative
*Neuroblastoma - 2 lines negative
*Teratocarcinoma - 3 lines negative
*Lymphoid - 6 lines negative Normal:
Human Kidney - 3/13 lines have 10% positive cells.
(from human patients)
Human Fibroblasts - 6 lines negative.
(from human patients)

*Melanoma: Monette
Murawaski
MIWO
Weinberg
Wolffe
Effrom
Arnonsky
Abenson

Astrocytoma: U373
AJ
AS
BE

Neuroblastoma: SK-NM
SK-N-Be(2)

Lymphoid: RAJI
DAUDI
T-45
MOLT-4
Moross B cells
Blau B cells

Teratocarcinoma:
Tera 1
Tera 2
SVCC

TABLE IV
Distribution of Antigens on Kidney Nephron

| | Glomerulus | Proximal Tubule | Loop of Henle | Distal Tubule | Collecting Tubule |
|---|---|---|---|---|---|
| AJ8 | | * | * | * | * |
| | | * | * | * | * |
| S$_4$ | | * | * | * | * |
| | | * | * | * | * |
| F$_{23}$ | | * | * | * | * |
| | | * | * | * | * |
| S$_{23}$ | | * | * | * | * |
| | | * | * | * | * |
| S$_{27}$ | | * | * | * | * |
| | | * | * | * | * |
| F$_{31}$ | | * | * | * | * |
| | | | | * | * |

Area of Overlap

Legend to Table IV:
Table IV diagrams the region of reactivity of the monoclonal antibodies AJ8, S$_4$, F$_{23}$, S$_{23}$, S$_{27}$ and F$_{31}$ with the regions of the kidney nephron namely, the glomerulus, proximal tubule, Loop of Henle, distal tubule, and collecting tubule:
AJ8 and S$_4$ mAbs react with glomerular tissue as well as most proximal tubule tissue extending almost to the loop of Henle.
F$_{23}$ mAb does not react with glomerular cells but only with proximal tubular cells.
S$_{23}$ mAb also does not react with glomerular cells but with cells the length of the proximal tubule and extending somewhat into the loop of Henle.
S$_{27}$ mAb does not react with glomerular cells but with cells extending the length of the proximal tubule and extending somewhat into the loop of Henle.
F$_{31}$ mAb does not react with cells of the glomerulus nor with cells along most of the length of the proximal tubule but only with cells at the distal end of the proximal tubule and with cells further along the length of the Loop of Henle than S$_{27}$.

Thus the area of overlap in the invention is the distal end of the proximal tubule together with that portion of the Henle closely adjacent to the proximal tubule. This seems to be where most renal carcinomas arise. Since 80% of renal carcinomas appear to co-express some of the antigens of the proximal tubule (S$_4$ and/or S$_{23}$ and/or F$_{23}$ and/or S$_{27}$) as well as the antigen defined by F$_{31}$, it appears that most renal carcinomas are derived from the small area of overlap of this group of antigens, that is at the distal aspect of the proximal tubule.

This is generally a critical area of the development of the nephron.

While the cells of the proximal tubule and the Loop of Henle are derived from the same embryologic stem cells they differentiate into cells which perform different fuctions and it is at the junction of where these two diversity differentiated cell types exist that the tumors arise.

Looking at the above results one can see that it is not always possible to predict successful hybridoma preparation of one cell line although success may have been achieved with another cell line. Any new cell line is impossible to predict because of the vagaries of the art of monoclonal antibodies. Preparation of hybrid cell lines can be successful or not depending on such experimental factors as nature of the innoculant, cell growth conditions, hybridization conditions and the like.

Normal proximal tubule cells express gp antigens at consistent levels (gp 160, gp120r and gp115) whereas only 5/31 tumors expressed all three antigens. 26 tumors did not express these antigens and 8 of the tumor cell lines tested were negative for gp140. In further differentiating normal versus malignant cells it is noted that when one of the gp antigens (160, 120r or 115) *was* present in a tumor levels of expression of the antigen ranged as high as 10,000 x normal. Results show antigen expression correlates with the malignant potential of these tumors.

MAbs S22, S23, S27 and S4 prepared from SK-RC-7 immunogen and $F_{31}$ prepared from SK-RC-1 immunogen are used to subset the nephron and identify antigenically and clinically distinct subtypes of renal carcinoma using immunopathological techniques. Approximately, 80% of RC appear to be $F_{31}$+. These tumors probably arise from the area of overlap of $F_{31}$ with other antigens of RC. These examples using specific mAb, renal carcinoma and methods are illustrative of the invention and are not meant to limit it.

Frozen sections of 55 renal cancer (RC) specimens are typed with the four mAbs ($S_4$, $S_{22}$, $S_{23}$ and $S_{27}$) using standard immunofluorescence and peroxidase techniques. (Table V) The mAbs detect four antigenic systems. gp120r, gp120nr and gp160 are glycoprotein differentiation antigens of proximal tubule (PT). gp115 is found only on renal cancer cells.

Subsets of RC can be identified on the basis of antigen expression at two levels. First, gp120nr expression separates a major group which is positive (51 in number) from a minor group which is negative (4 in number). Of gp120nr+RC, 41 (82%) express at least 2 of the PT differentiation markers, consistent with the traditional view that RC is derived from PT. The four gp120nr-RC lack expression of the 3 PT markers (P less than 0.01) suggesting derivation from other parts of the nephron. Second, the gp120nr+group can be divided into eight subsets, defined by (+) or (−) expression of gp160, gp120r and gp115 (Table IV).

Contrary to the apparent coordinate lack of expression of these antigens in the gp120nr- subgroup, the gp120nr+RC demonstrate incoordinate, independent expression. Subsets of RC defined in this way may differ in their clinical course.

TABLE V

Renal Carcinoma Typing Using Monoclonal Antibody

| Patient # | Chart | Renal Pathol. | Surg. Date | Stage | Met Site | S4 | S22 | S23 | S27 |
|---|---|---|---|---|---|---|---|---|---|
| 1 | 785198 | 816328 | 0481 | 1 | | + | ± | + | + |
| 2 | 808371 | 8218413 | 1082 | 1 | | + | − | + | + |
| 3 | 799223 | 824878 | 0382 | 1 | | + | − | − | + |
| 4 | 791203 | 8115565 | 0881 | 1 | | + | − | − | + |
| 5 | 736676 | 818362 | 0581 | 1 | | − | − | + | + |
| 6 | 812434 | 83578 | 0182 | 1 | | + | − | + | + |
| 7 | 797121 | 822197 | 0282 | 1 | | + | − | + | + |
| 8 | 992833 | 8118815 | 1081 | 1 | | − | − | + | + |
| 9 | 572899 | 829219 | 0582 | 1 | | − | + | + | + |
| 10 | 991626 | 8116180 | 0981 | 1 | | − | − | − | − |
| 11 | 810260 | 822093 | 1182 | 1 | | + | ± | + | + |
| 12 | 799817 | 8113368 | 0781 | 1 | | + | − | − | + |
| 13 | 796815 | 82773 | 0182 | 1 | | + | − | − | + |
| 14 | 787807 | 8116150 | 0981 | 2 | | + | ± | + | + |
| 15 | 787964 | 8110339 | 0681 | 2 | | + | − | − | + |
| 16 | 788328 | 8110924 | 0681 | 2 | | − | ± | + | + |
| 17 | 798926 | 823741 | 0382 | 2 | | + | − | + | + |
| 18 | 543708 | 824937 | 0382 | 2 | | + | ± | − | + |
| 19 | 643512 | 823179 | | 2 | | + | ± | + | + |
| 20 | 991637 | 8116440 | 0981 | 2 | | − | − | − | + |
| 21 | 792783 | 8121194 | 1181 | 2 | | + | ± | + | + |
| 22 | 801696 | 827564 | 0482 | 4 | | − | − | − | − |
| 23 | 799512 | 824468 | 0382 | 2 | | + | ± | + | + |
| 24 | 787183 | 819786 | 0681 | 2 | | + | + | + | + |
| 25 | 802482 | 8210362 | 0682 | 3 | | + | − | − | + |
| 26 | 795288 | 8122239 | 1281 | 3 | | − | + | − | + |
| 27 | 790003 | 8114712 | 0881 | 4 | | − | − | − | + |
| 28 | 784799 | 815643 | 0481 | 4 | | − | − | − | + |
| 29 | 788722 | 811186 | 0681 | 4 | | − | − | − | + |
| 30 | 786021 | 819070 | 0581 | 4 | | + | + | + | + |
| 31 | 802850 | 829377 | 0582 | 4 | | + | − | − | + |
| 32 | 784690 | 816654 | 0481 | 4 | | + | − | − | + |
| 33 | 787833 | 8110396 | 0681 | 4 | | − | − | − | + |
| 34 | 991686 | 8117874 | 1081 | 4 | | − | + | − | + |
| 35 | 806154 | 8215512 | 0882 | 4 | | − | − | − | − |
| 36 | 784902 | 816649 | 0481 | 3 | | − | + | + | + |
| 37 | 993395 | 8215363 | 0882 | 1 | | + | − | + | + |
| 38 | 993395 | 832130 | 0283 | 2 | | + | − | + | + |
| 39 | 738554 | 0 | 1082 | 4 | | − | − | + | + |
| 40 | 738554 | 0 | 1182 | 4 | | − | − | + | + |
| 41 | 738554 | 0 | 1282 | 4 | SKULL | − | − | + | + |
| 42 | 0 | 806807 | 1082 | 2 | | + | − | + | + |
| 43 | 794184 | 8222885 | | 4 | SKIN | − | + | + | + |
| 44 | 794184 | 0 | | 4 | SKIN | − | + | + | + |
| 45 | 794184 | 0 | | 4 | SKIN | − | + | + | + |
| 46 | 654004 | 818164 | 0581 | 4 | BONE | + | ± | − | + |
| 47 | 654004 | 0 | | 4 | BONE | + | ± | − | + |
| 48 | 794954 | 829571 | 0582 | 4 | BRAIN | + | − | − | + |
| 49 | 785655 | 816867 | 0481 | 4 | BONE | + | − | − | + |
| 50 | 791592 | 8116033 | 0981 | 4 | BONE | + | − | − | + |
| 51 | 786081 | 8111741 | 0781 | 4 | BONE | − | ± | − | + |
| 52 | 991879 | 823468 | 0382 | 4 | LUNG | + | − | + | + |
| 53 | 808557 | 8219016 | 1082 | 4 | NODES | − | − | − | + |
| 54 | 814996 | 838182 | 0283 | 4 | | + | − | − | + |

TABLE V-continued

Renal Carcinoma Typing Using Monoclonal Antibody

| Patient # | Chart | Renal Pathol. | Surg. Date | Stage | Met Site | S4 | S22 | S23 | S27 |
|---|---|---|---|---|---|---|---|---|---|
| 55 | 807399 | 8216668 | 0982 | 4 | | − | − | − | + |

Legend to Table V:
Frozen sections of renal carcinoma (RC) specimens are typed with the four mouse monoclonal antibodies $S_4$, $S_{22}$, $S_{23}$ and $S_{27}$ (derived from SK-RC-7 immunizing cell line) using standard immunofluorescence and peroxidase techniques.
Met Site = site of metastisis specimen
+ = positive reaction
− = negative reaction
± = heterogeneous reaction
Patient also 39, 40 and 41 concern different tissue specimens from the same patent i.e. different sites. This applies to 46, 47 and 48 as well.

14/16 gp120r+/gp160+RC were localized to the kidney (p less than 0.001), whereas 9/9 gp120r−/gp160− tumors were disseminated (less than 0.01) and developed at an earlier median age (44 vs. 57 years, p less than 0.01). These mAbs including $F_{31}$ are useful in defining the histiogenesis, diagnosis and prognosis of RC subsets.

TABLE IV

| gp 120nr+ Subsets | | | | | | | | |
|---|---|---|---|---|---|---|---|---|
| gp 160 type | + | + | + | − | − | + | − | − |
| gp 115 type | + | − | + | + | + | − | − | − |
| gp 120r type | + | − | − | − | + | + | − | + |

The above examples are for illustrative purposes only and are not meant to limit the scope of the invention. It is obvious that the invention also encompasses all monoclonal antibodies and RC possessing the same characteristics as described herein. The examples do not limit the invention especially with respect to substantially functional equivalents of hybridomas, monoclonal antibodies, RC, cell lines and methods described and claimed herein.

Changes in cell antigens are associated with different stages of differentiation and different stages of cancer. Thus this invention technique defines cell antigens associated with differentiation and cancer of the kidney and its associated tubules. Localization of the area associated with most RC is highlighted by the new mAb $F_{31}$ as well as the renal panel of $F_{23}$, $S_{23}$ and $S_{27}$.

The antibodies and methods discussed subset the nephron and subset renal cancers. These methods are clinically useful to diagnose renal cancer, to describe the histiogenesis and prognosis of renal cancer, as well as to treat RC.

The following hybridoma lines are maintained on deposit at Sloan-Kettering Institute for Cancer Research, 1275 York Avenue, New York, N.Y. 10021 under designations corresponding to the mAb produced by each hybridoma as follows $S_4$, $S_{22}$, $S_{23}$, $S_{27}$ and $F_{31}$.

Said hybridoma lines have been deposited with the American Type Culture Collection (ATCC) 12301 Parklawn Drive, Rockville, Md. 20852 under ATCC designations corresponding to the above Sloan-Kettering designations as follows:

| | Deposit date | Corresponding ATCC Accession No. |
|---|---|---|
| $F_{31}$ | April 24, 1984 | HB8548 |
| $S_4$ | April 17, 1984 | HB8541 |
| $S_{22}$ | April 17, 1984 | HB8542 |
| $S_{23}$ | April 17, 1984 | HB8540 |
| $S_{27}$ | November 15, 1983 | HB8428 |
| $F_{23}$ | March 11, 1983 | HB8231 |

Immunizing cell lines SK-RC-7 and SK-RC-1 are also on deposit and available at Sloan-Kettering Institute.

Immunizing cell lines SK-RC-7 and SK-RC-1 have been deposited with the ATCC on May 4, 1984 and have been given ATCC designations CRL-8559 and CRL8560 respectively.

What is claimed is:

1. Monoclonal antibody panel derived from human renal carcinoma or normal epithelial antigen useful for diagnosing renal cancers in humans by recognizing with overlapping reactivity a site of origin of most renal carcinomas comprising the distal end of the renal proximal tubule (pars recta) and adjacent portion thereto of the Loop of Henle and wherein the panel consists of monoclonal antibody $S_4$ (HB 8541), $S_{23}$ (HB 8540), $F_{23}$ (HB 8231), $S_{27}$ (HB 8428) and $F_{31}$ (HB 8548).

2. Hybridoma cell line producing a monoclonal antibody $F_{31}$ (HB 8548).

3. Monoclonal antibody $F_{31}$ (HB 8548) capable of reaction with 80% of renal carcinomas and recognizing a site of origin of most renal carcinomas comprising the distal end of the renal proximal tubule and adjacent portion thereto of the Loop of Henle.

4. Method for detecting malignant human renal cells which comprises contacting a human renal specimen with each of the monoclonal antibodies of the monoclonal antibody panel of claim 1 which have been labeled with a fluorescent of radioactive agent and identifying malignant renal cells in the distal end of the proximal tubule and the adjacent portion of the loop of Henle.

5. Method for detecting malignant human renal cells which comprises contacting a human renal specimen with each of the monoclonal antibodies of the monoclonal antibody panel of claim 1, and identifying malignant renal cells in the distal end of the proximal tubule and the adjacent portion of the loop of Henle by an indirect immunofluorescent assay.

* * * * *